US00RE34656E

United States Patent [19]

Golub et al.

[11] E Patent Number: Re. 34,656

[45] Reissued Date of Patent: Jul. 5, 1994

[54] USE OF TETRACYCLINE TO ENHANCE BONE PROTEIN SYNTHESIS AND/OR TREATMENT OF BONE DEFICIENCY

[75] Inventors: Lorne M. Golub, Smithtown; Thomas F. McNamara, Port Jefferson; Nungavaram S. Ramamurthy, Smithtown, all of N.Y.

[73] Assignee: The Research Foundation of State University of New York, Albany, N.Y.

[21] Appl. No.: 878,172

[22] Filed: May 4, 1992

Related U.S. Patent Documents

Reissue of:

[64] Patent No.: 4,925,833
Issued: May 15, 1990
Appl. No.: 946,726
Filed: Dec. 29, 1986

U.S. Applications:

[63] Continuation-in-part of Ser. No. 699,048, Feb. 7, 1985, Pat. No. 4,704,383, which is a continuation-in-part of Ser. No. 566,517, Dec. 29, 1983, Pat. No. 4,666,897.

[51] Int. Cl.[5] ..... A61K 31/65

[52] U.S. Cl. ..... 514/152; 514/899

[58] Field of Search ..... 514/152

[56] References Cited

U.S. PATENT DOCUMENTS

| | | |
|---|---|---|
| 2,895,880 | 7/1959 | Rosenthal . |
| 3,304,227 | 2/1967 | Loveless . |
| 3,636,202 | 1/1972 | Klein . |
| 3,914,299 | 10/1975 | Muxfeldt . |
| 4,248,892 | 2/1981 | Kanamaru et al. . |
| 4,276,284 | 6/1981 | Brown . |
| 4,371,465 | 2/1983 | McGregor . |
| 4,454,110 | 6/1984 | Cáslavsk et al. . |
| 4,457,936 | 7/1984 | Draeger et al. . |
| 4,666,897 | 5/1987 | Golub et al. . |
| 4,704,383 | 11/1987 | McNamara et al. . |
| 4,925,833 | 5/1990 | Golub et al. . |
| 4,935,411 | 6/1990 | McNamara et al. . |
| 4,935,412 | 6/1990 | McNamara et al. . |

FOREIGN PATENT DOCUMENTS

| | | |
|---|---|---|
| 787882 | 12/1957 | United Kingdom . |
| 925282 | 5/1963 | United Kingdom . |

OTHER PUBLICATIONS

Golub, et al., *Chemical Abstracts*, 100:96203a, (1984).
Engesaeter, et al., *Chemical Abstracts*, 93:142977t, (1980).
Smirnov, I. V., *Chemical Abstracts*, 76:30596, (1969).
Valcavi, et al., *Chemical Abstracts*, 95:6899h, (1981).
Brandt, et al., *Chemical Abstracts*, 92:163746m, (1979).
Glantz, et al., *Chemical Abstracts*, 91:20178w, (1979).
Muxfeldt, *Chemical Abstracts*, 76:140344j, (1972).
Bitha, et al., *Chemical Abstracts*, 72:43253P, (1970).
Myl'nikova, *Chemical Abstracts*, 86:66138h, (1976).
Plakunov, *Chemical Abstracts*, 80:104410b, (1973).
Dreisbach, et al., "Induction of Collagenase Production in Vibrio B—30", *J. Bacteriology*, vol. 135, No. 2, pp. 521-527, (1978).
Goodman and Gilman, *The Pharmacological Basis of Therapeutics*, 6th edition, p. 961-2, (1980).
Perry, et al., "Systemic Tetracycline in the Treatment of Non-Infected Corneal Ulcers and Persistent Epithelial Defects", *J. Period Res.* 83:20, 185-195 (Abstract and Artide) (1984).
Gomes, et al., "Tetracyclines Inhibit Parathyroid Hormone-Induced Bone Resorption in Organ Culture", (List continued on next page.)

*Primary Examiner*—Marianne M. Cintins
*Assistant Examiner*—T. J. Criares
*Attorney, Agent, or Firm*—Hoffmann & Baron

[57] ABSTRACT

Tetracyclines, antibacterial and non-antibacterial tetracyclines, have been found to be useful in the treatment of osteoporosis in humans by administering to the human suffering from osteoporosis an effective amount of a tetracycline to enhance bone protein synthesis. Tetracyclines which have been found to be effective in the treatment of osteoporosis in humans include minocycline, doxycycline and dedimethylaminotetracyline.

20 Claims, No Drawings

OTHER PUBLICATIONS

School of Dental Medicine Study, SUNY, (Mar. 19, 1984).

Goodson, et al., "Monolithic Tetracycline-containing Fibers for Controlled Delivery to Periodontal Pockets", *J. Periodontol.* 54 575-579 (Jan. 1983).

"Anti-Plaque Agents", *Pharmacy Times*, 97 (Jul. 1985).

"Periodontal Disease Research, Guide to Dental Health", *Journal of the American Dental Association*, 70-74 (1985).

"British Bio-Technology Group's Collagenase Inhibitor Adjunctive", *F-D-C Reports*, Inc., 13 (1983).

ALZA/P&G Periodontal Disease Partnership:Actisite, *F-D-C Reports*, Inc., 8-9 (1990).

"Zyderm Collagen Treatments", Collagen Corporation, Advertisement, (Dec. 1981).

O'Donovan, J. P., "A Chick Screen to Evaluate Chemical Compounds from Janssen Pharmaceutical for Growth Promotion", Chick Growth Promotion Screen Report (1987).

Katz, S. E., "Is Today's Meat Fit to Eat?", *Chemical and Engineering News*, 80-81 (Mar. 11, 1985).

Golub, et al., "Minocycline Therapy Reduces Gingival Collagenolytic Enzyme Activity During Diabetes: A Proposed New Mechanism of Action, *J. Of Periodontal Research*", 18: 516-526, Abstract, (1983).

Golub, et al., "Minocycline Reduces Gingival Collagenolytic Activity During Diabetes", *Journal of Periodontal Research*, 18: 516-526 (1983).

Golub, et al., "Minocycline Therapy Inhibits the Abnormal Gingival Collagenolytic Activity During Experimental Diabetes", *Journal of Dental Research*, 62:290, Abstract 1085, (1983).

Williams et al., "Tetracycline Treatment of Periodontal Disease in the Beagle Dog:", *Journal of Periodontal Research*, 16:555-674, (1981).

Brown et al., "Rheumatoid Artritis in the Gorilla:A Study of Mycoplasma-Host Interaction in Pathogenesis and Treatment", *Comarative Pathology of Zoo Animals*, 259-266, (1980).

Berman, M. B., "Collagenase and Corneal Ulceration", 8:141-174, (1980).

Addy, et al., "The Development and in Vitro Evaluation of Acrylic Strips and Dialysis Tubing for Local Drug Delivery", *J. Periodonal*, 693-699, (Nov. 1982).

Addy, et al., "Comparison of the Immediate Effects on the Subgingival Microflora of Acrylic Strips Containing 40% Chlorhexdine, Metronidazole or Tetracycline", *Journal of Clinical Periodontology*, 11:379-386, (1984).

Sheridan, P., "Tetracyclines Block Collagenase Activity", *JAMA*, 252, 1989-1990 (Oct. 19, 1984).

USE OF TETRACYCLINE TO ENHANCE BONE PROTEIN SYNTHESIS AND/OR TREATMENT OF BONE DEFICIENCY

Matter enclosed in heavy brackets [ ] appears in the original patent but forms no part of this reissue specification; matter printed in italics indicates the additions made by reissue.

This application is a continuation-in-part application of copending, coassigned patent application Ser. No. 699,048 filed Feb. 7, 1985, now U.S. Pat. No. 4,704,383 which in turn, is a continuation-in-part of copending, coassigned patent application Ser. No. 566,517 filed Dec. 29, 1983, now U.S. Pat. No. 4,666,897.

The disclosures of the above-identified applications are herein incorporated and made part of this disclosure.

BACKGROUND OF THE INVENTION

In pending U.S. patent application Ser. No. 566,517, now U.S. Pat. No. 4,666,897, it is disclosed that tetracyclines, such as the antibiotic tetracyclines, e.g. tetracycline, are useful as anti-collagenolytic agents or as inhibitors of collagenase. These tetracyclines and compositions containing the same are disclosed therein as being useful in the treatment of periodontal diseases, corneal ulcers, rheumatoid arthritis and the like characterized by excessive collagen destruction.

In pending U.S. patent application Ser. No. 699,048, now U.S. Pat. No. 4,704,383, it is disclosed that the non-antibiotic or non-antibacterial tetracyclines also possess anti-collagenolytic properties and are useful as inhibitors of collagenase. Additionally, these non-antibiotic or non-antibacterial tetracyclines have also been found to be useful in the treatment of periodontal diseases, corneal ulcers, bone deficiency disorders due to excess collagenase production or excessivde collagen destruction, rheeumatoid arthristis and the like. A particularly useful non-antibiotic tetracycline in the practices of this invention is the tetracycline dedimethylaminotetracycline.

Tetracyclines are useful as broad spectrum antibiotics because they have the ability to inhibit protein synthesis in a wide variety of bacteria. As disclosed in the above-identified pending patent applications, it has also been discovered that tetracyclines, antibiotic tetracyclines and non-antibiotic tetracyclines, have th ability to inhibit collagen-destructive enzymes, such as collagenase, responsiple for the breakdown of connective tissue in a number of diseases, such as periodontal disease, corneal ulcers and rheumatoid arthritis.

SUMMARY OF THE INVENTION

It has been discovered that inhibitors of collagen-destructive enzymes, such as collagenase, are useful in the treatment of mammals, such as humans, to prevent the development of osteoporosis and/or to stimulate bone protein synthesis. In the practices of this invention an effective amount of a physiologically acceptable collagenase inhibitor is systemically administered to the mammal or human to bring about the stimulation of bone protein synthesis or to treat bone deficiency disease or osteoporosis. The amount of the inhibitor administered to the mammal or human can be at a therapeutic level, i.e. substantially the same dosage as would be employed in the treatment of barterial infections and the like, or at a reduced, subtherapeutic level, in the range about 5–60% of the therapeutic dosage. The amount administered in accordance with the practices of this invention would be effective to inhibit the collagen-destructive enzymes, such as collagenase, in the mammal, e.g. subject to which the inhibitor is administered.

More particularly, it has been discovered that tetracyclines, antibacterial and non-antibacterial tetracyclines, which are inhibitors of collagenase, enhance or stimulate bone protein synthesis and have been found to be useful in the treatment of osteoporosis in humans. In the light of the discovery of this invention that tetracyclines stimulate and enhance bone protein synthesis, tetracyclines have been found to be useful in the treatment of osteoporosis.

DETAILED DESCRIPTION OF THE INVENTION

The following disclosures of examples are illustrative of the practices of this invention.

EXAMPLE NO. 1

In this experiment 4 groups of adult male rats were set up, viz, a group of normal rats which served as controls, a group of rats that were rendered diabetic by streptozotocin administration and two additional groups of diabetic rats, one of which was administered by oral intubation 20 mg per day of a chemically modified non-antibiotic tetracycline (CMT), and the other of which was orally administered 5 mg per day of minocycline, a semi-synthetic commercially available antibiotic tetracycline. Each of the 4 groups of rats contained 4 rats each. Three weeks after beginning the experiment, but 2 hours before sacrifice, each rat was injected with 1 mCi of $H^3$-proline to radioactively label the newly synthesized protein in the skeletal and other tissues. After the rats were killed, the long bones were removed, cleaned free of soft tissue, the mid-shaft of the cleaned bone collected and hydrolyzed in 6N HCl (24 h, 105° C.), and an aliquot measured in a liquid scinitillation spectrometer after evaporating the acid. The data on bone protein synthesis is shown in Table 1.

TABLE I

The administration of minocycline or chemically-modified non-antibiotic tetracycline (CMT) to diabetic rats: effect on bone protein systhesis in vivo

| Experimental Group | Bone Protein synthesis (DPM $H^3$-Pro/mg bone tissue) |
|---|---|
| Controls | 886 ± 155 |
| Diabetics (D) | 588 ± 89 |
| D + minocycline | 852 ± 145 |
| D + CMT | 828 ± 248 |

Inducing diabetes in the rat suppressed protein synthesis in the skeletal tissue; after months of this metabolic dysfunction in the bones, they developed physically and chemically-detectable bone-deficiency disease. When either of the two tetracyclines was orally administered to the diabetics, bone protein synthesis was increased to essentially normal values, and this metabolic alteration was associated with the prevention of the devleopment of osteoporosis.

EXAMPLE NO. 2

In this experiment 3 groups of animals were established: a group of non-diabetic controls, a group of untreated diabetics, and a group of diabetic rats that were administered, by the oral route, 1.5 mg doxycycline, an antibiotic tetracycline, per day for the entire 3½ month experimental period. After 3.5 months, the rats were killed, the bones (femur and tibia) were removed, defleshed, and radiographs taken. Physical and biochemical parameters were also measured. Other bones (mandible) were processed for light microscopy. Diabetes significantly reduced the dry weight, density, ash, matrix, calcium and hydroxyproline content of the skeletal tissue (the unchanged Ca/Hyp ratio indicated the bone was normally calcified even through osteopenic). Long-term doxycycline therapy retarded the loss of organic and inorganic bone constituents in the diabetics even though the severity of hyperglycemia was unaffected. Radiographic changes were consistent with the above findings. In short-term studies, treatment of diabetic rats with a different tetracycline (minocycline) showed a similar pattern of results. Tetracycline therapy in rats retarded osteoporotic changes in bone induced by diabetes.

It was observed that untreated diabetic rats developed bone deficiency disease, or osteoporosis, based on physical, radiologic, chemical and histologic assessments. However, the tetracycline, doxycycline, therapy prevented the development of diabetes-induced osteoporosis even though the drug had no effect on the severity of the diabetic state, presumably because the drug increased the depressed protein synthesis in the skeletal tissues.

EXAMPLE NO. 3

TABLE II

Effects of CMT Administration (20 mg per day) on Urinary Calcium Excretion in Streptozotocum-Diabetic Rats

| Experimental Group | Number of Rats per Group | μg Ca m urine per 24 h* |
|---|---|---|
| Control | 4 | 33 ± 5 |
| Diabetes | 4 | 691 ± 35 |
| Diabetes + CMT | 4 | 398 ± 33 |

Each value represents the mean ± S.E.M. of 12 volumes: a 24 h determination was made for each rat (n = 4 per group), on days 18, 19 and 20 after reducing diabetes The results shown above in Table II summarizes the reduction in calcium excretion in the diabetic animals treated with CMT as compared with the untreated diabetic animals. Diabetes dramatically increases the urinary excretion of calcium compared with control values and an elevated urinary excretion of calcium is associated with the development of osteoporosis. Administration of CMT to the diabetic animals reduced the pathologically excessive excretion of calcium by 42%; this is biochemical evidence of the amelioration of the condition resulting from the administration of CMT.

EXAMPLE NO. 4

Tetracycline can inhibit tissue degradation by anti-collagenase action and has reduced pathological bone resorption through this mechanism (Golub et al. 1983, 84). A study was undertaken to evaluate whether tetracycline could have any discernible effect upon morphologic characteristics of bone undergoing nomral remodeling. Four squirrel monkeys received a daily dose of tetracycline at 100 mg/kg/day given by oral intubation in 3 equal doses. After 17 days of tetracycline administration the animals were sacrificed and the jaws processed for histologic sectioning. Bucco-lingual sections were prepared from bicuspid and cuspid teeth. A defined coronal buccal alveolar bone region was analyzed histologically and histometrically using step-serial sections. Corresponding regions were analyzed from bicuspids and cuspids from 4 animals which had not received tetracycline administration. Morphologic characteristics of the bone were analyzed using a Bioquant computerized digitization system, and comparisons made between the groups. Within the defined region, the total area of alveolar bone and the number of marrow spaces, did not differ between the two groups. However, the area of the narrow spaces was significantly less in tetracycline-receiving animals. The marrow spaces occupied 0.5±0.09(SE)% of the bone in tetracycline-receiving animals, in contrast to the 7.9±1.2(SE)% ($t=3.49$, $p<0.01$) present in control animals. In the tetracycline-receiving animals, the marrow spaces appeared to be lined by new bone, as were the periodontal ligament surfaces of the alveolar bone. The increased bone density may have been due to inhibition of resorption without affecting the deposition phase of bone remodeling.

Although in the practices of this invention many compounds, particularly physiologically acceptable collagenase inhibitors, are useful, it is preferred to employ a tetracycline antibiotic or non-antibiotic. Tetracyclines, broadly, can be characterized as containing four fused carbcyclic groups. This arrangement appears to be characteristic of compounds which are collagenase inhibitors and which are also useful in the practices of this invention. Related compounds, compounds which are related as analogs or homologs of tetracycline, are also useful as well as compounds which are characterized as having three fused carbocyclic groups. Suitable such compounds are disclosed herein and include 7-chlorotetracycline, 5-hydroxytetracycline, 6-demethyl-7-chlorotetracycline, 6-demethyl,-6-deoxy-5-hydroxy-6-methylenetetracycline, 6-alpha-benzylthiomethylenetetracycline, a nitrile analog of tetracycline, a mono-N-alkylated amide of tetracycline, 6-fluorodemethyltetracycline, 11-alpha-chlorotetracycline, 2-acetyl-8-hydroxy-1-tetracycline and 6-demethyl-6-deoxytetracycline.

As mentioned hereinabove, the compounds employed in the practices of this invention are employed in an effective amount for the treatment of osteoporosis, such as an amount effective to enhance the synthesis of bone protein and/or correct to treat any deficiency disease. The amount employed depends to some extent upon the body weight of the mammal or human being treated. With respect to humans, the amount employed, particularly in the case of compounds which are collagenase inhibitors and/or characterized as being a tetracycline, on a daily dosage, it is usually less than about 400 milligrams and usually below about 200 milligrams. A suitable daily dosage for a human would be in the range 10 milligrams to about 50 milligrams for the treatment of osteoporosis or other bone deficiency disease and for the enhancement of the synthesis of bone protein.

As will be apparent to those skilled in the art in the light of the foregoing disclosure, many alterations, substitutions and modifications are possible in the practices of this invention without departing from the spirit or scope thereof.

What is claimed is:

1. [A] *The* method of [enhancing bone protein synthesis in a human which comprises administering to the human an effective amount of a tetracycline] *claim 20 wherein said disease is osteoporosis*.

2. A method in accordance with claim [1] *20* wherein said tetracycline is an antibacterial tetracycline.

3. A method in accordance with claim [1] *20* wherein said tetracycline is non-antibacterial tetracycline.

4. A method in accordance with claim [1] *20* wherein said tetracycline is minocycline.

5. A method in accordance with claim [1] *20* wherein said tetracycline is doxycycline.

6. A method in accordance with claim [1] *20* wherein said tetracycline is 7-chlorotetracycline.

7. A method in accordance with claim [1] *20* wherein said tetracycline is 5-hydroxytetracycline.

8. A method in accordance with claim [1] *20* wherein said tetracycline is 6-demethyl-7-chlorotetracycline.

9. A method in accordance with claim [1] *20* wherein said tetracycline is 6-demethyl-6-deoxy-5-hydroxy-6-methylenetetracycline.

10. A method in accordance with claim [1] *20* wherein said tetracycline is dedimethylaminotetracycline.

11. A method in accordance with claim [1] *20* wherein said tetracycline is 6-alpha-benzylthiomethylenetetracycline.

12. A method in accordance with claim [1] *20* where said tetracycline is a nitrile analog of tetracycline.

13. A method in accordance with claim [1] *20* wherein said tetracycline is a mono-N-alkylated amide of tetracycline.

14. A method in accordance with claim [1] *20* wherein said tetracycline is 6-fluorodemethyltetracycline.

15. A method in accordance with claim [1] *20* wherein said tetracycline is 11-alpha-chlorotetracycline.

16. A method in accordance with claim [1] *20* wherein said tetracycline is 2-acetyl-8-hydroxyl-1-tetracycline.

17. A method in accordance with claim [1] *20* wherein said tetracycline is 6-demethyl-6-deoxytetracycline.

18. A method in accordance with claim [1] *20* wherein said tetracycline is administered systemically.

19. A method in accordance with claim [1] *20* wherein said tetracycline is administered orally.

20. *A method of treating mammal with bone deficiency disease by enhancing bone protein synthesis in said mammal which comprises administering to the mammal an effective amount of a tetracycline.*

* * * * *

US00RE34656F1

(12) EX PARTE REEXAMINATION CERTIFICATE (5258th)

United States Patent

Golub et al.

(10) Number: US RE34,656 C2

(45) Certificate Issued: Jan. 17, 2006

(54) USE OF TETRACYCLINE TO ENHANCE BONE PROTEIN SYNTHESIS AND/OR TREATMENT OF BONE DEFICIENCY

(75) Inventors: Lorne M. Golub, Smithtown, NY (US); Thomas F. McNamara, Port Jefferson, NY (US); Nungavaram S. Ramamurthy, Smithtown, NY (US)

(73) Assignee: The Broadway Research Foundation of State University of New York, Albany, NY (US)

Reexamination Request:
No. 90/006,753, Aug. 19, 2003

Reexamination Certificate for:

| | |
|---|---|
| Patent No.: | **1,034,656** |
| Issued: | **Jul. 5, 1994** |
| Appl. No.: | **07/878,172** |
| Filed: | **May 4, 1992** |

Reexamination Certificate B1 Re. 34,656 issued May 15, 1990

Related U.S. Patent Documents

Reissue of:

| | |
|---|---|
| (64) Patent No.: | **4,925,833** |
| Issued: | **May 15, 1990** |
| Appl. No.: | **06/946,726** |
| Filed: | **Dec. 29, 1986** |

Related U.S. Application Data

(63) Continuation-in-part of application No. 06/699,048, filed on Feb. 7, 1985, now Pat. No. 4,704,383, which is a continuation-in-part of application No. 06/566,517, filed on Dec. 29, 1983, now Pat. No. 4,666,897.

(51) Int. Cl.
*A61K 31/65* (2006.01)

(52) U.S. Cl. ..... 514/152; 514/899

(58) Field of Classification Search ..... 514/152
See application file for complete search history.

(56) References Cited

U.S. PATENT DOCUMENTS

| | | | | |
|---|---|---|---|---|
| 2,895,880 | A | | 7/1959 | Rosenthal |
| 3,304,227 | A | | 2/1967 | Loveless |
| 3,636,202 | A | | 1/1972 | Klein |
| 3,914,299 | A | | 10/1975 | Muxfeldt |
| 4,248,892 | A | | 2/1981 | Kanamaru et al. |
| 4,256,743 | A | * | 3/1981 | Goldhaber ..... 514/226.2 |
| 4,276,284 | A | | 6/1981 | Brown |
| 4,371,465 | A | | 2/1983 | McGregor |
| 4,391,824 | A | * | 7/1983 | Siuta et al. ..... 514/577 |
| 4,454,110 | A | | 6/1984 | Cáslavsk et al. |
| 4,457,936 | A | | 7/1984 | Draeger et al. |
| 4,666,897 | A | | 5/1987 | Golub et al. |
| 4,704,383 | A | | 11/1987 | McNamara et al. |
| 4,925,833 | A | | 5/1990 | Golub et al. |
| 4,935,411 | A | | 6/1990 | McNamara et al. |
| 4,935,412 | A | | 6/1990 | McNamara et al. |

FOREIGN PATENT DOCUMENTS

| | | |
|---|---|---|
| GB | 787882 | 12/1957 |
| GB | 925282 | 5/1963 |

OTHER PUBLICATIONS

Fasciano et al., "Periodontal Regeneration with Long Term Tetracycline Therapy.", Quintessence International, 12(10), pp. 1018–1088, (Oct. 1981).*

Likins et al., "effect of Fluoride and Tetracycline on Alveolar Bone Resorption in the Rat." National Institute of Dental Research, NIH, p. 1832, (Jul. 1963).*

Mashimo et al., "In Vitro Evaluation of Antibiotics in the Treatment of Periodontal Disease." Pharmacol. Ther. Dent. vol. 6, pp. 45–56, (1981).*

McNamara et al, "Crevicular Fluid Studies of a Diabetic and Her Non–Diabetic Twin." Program and Abstracts of Papers, J. of Dental Research, Abstract 1038, vol. 58, Special Issue A (Jan. 1979).*

Williams et al , "Tetracycline Treatment of Periodontal Disease in the Beagle Dog." J. of Periodontal Research, vol. 17, pp. 358–365, (1982).*

Guerrant, "Chlortetracycline and Bone Demineralization in the Rachitic Rat." Proceedings of the Society for Experimental Biology and Medicine, vol. 113, pp. 268–270, (1963).*

Abud, et al., J "Doxycycline in Dental Infections," (Doxiciclina en infecciones odontologicas) *Odontologia Chilena*, 22(111):19–21 (Jan.–Jun. 1974). (Chile). (English Translation).

Bruno, et al., "Clinical Comparative Study between Rifamycin, Doxycycline and Amoxicillin in the Treatment of Odontogenic Bone Inflammation," (Indagine clinica comparative fra rifampicina, doxiciclina e amoxicillina nel trattamento degli osteofilammoni odontogeni) *Rivista Italliana Di Stomatologtia*, 51(7–8): 635–43 (1982). (Italy). (English Translation).

Bauer, et al., 1983, *J. Invest. Dermatol.*, 81:162–169.

Berman and Manabe, 1973, *Ann. Ophthalmol.*, Nov., p. 1193–1209.

Uitto, et al., 1984, *J. Oral. Path.*, 13:412–418.

Narayanan and Page, 1983, *Collagen Rel. Res.*, 3:33–64.

Vater, et al., 1978, *J. Clin. Invest.*, 62:987–992.

Cowen, et al., 1985, *Biochem. International*, 11:273–280.

Delaisse et al., 1985, *Biochem. Biophys. Res. Commun.*, 133:483–490.

(Continued)

*Primary Examiner*—Barbara P. Badio

(57) ABSTRACT

Tetracyclines, antibacterial and non-antibacterial tetracyclines, have been found to be useful in the treatment of osteoporosis in humans by administering to the human suffering from osteoporosis an effective amount of a tetracycline to enhance bone protein synthesis. Tetracyclines which have been found to be effective in the treatment of osteoporosis in humans include minocycline, doxycycline and dedimethylaminotetracyline.

OTHER PUBLICATIONS

Rosemberg, J. "Action of Doxycycline (Vibramycin) in Dental Diseases," (Acao da doxiciclina (vibramicina) em afeccoes odontologicas) *Revista da Associacao Paulista de Cirurgioes Dentista*, 23(2):55–61 (Mar.–Apr. 1969) (Brazil) (English Translation).
Gutierrez G. C. "Clinical Trial with the Use of Doxycycline in Dentristry," (Ensayo clinico con doxiciclina en odontoestomatologia) *Anales Espanoles de Odontoestomatologia*, 28(5):372–7 (Sep.–Oct. 1969) (Spain) (English Translation).
Pes, I "Treatment of Mouth Diseases with Doxicycline," (Trattamento di affezioni stomatologiche con doxiciclina) *Rivista Italiana di Stomatologia*, 26(9):691–5 (1971) (Italy) (English Translation).
Wedler, A "Topical Application of Oxytetracycline in the Treatment of Ulcerative Gingivitis and Stomatitis," (Miejscowe stosowanie oxyterracyny w leczeniu wrzodziejacego zapalenia dziasel I blony sluzowej jamy ustnej) *Czasopismo Stomatologiczne*, 25(1):103–12 (1972). (Poland) (English Translation).
Gangarosa et al., Pharmacotherapeutics in Dentistry, Chapter 28 ("Tetracycline") pp. 281–285, Appleton–Century–Crofts, publishers, Norwalk, Conn. (1983).
Sanders et al., Clinical Evaluation of Freeze–dried Bone Allografts in Periodontal Osseous Defects—Part III. Composite Freeze–Dried Bone Allografts With and Without Autogenous Bone Grafts, J. Periodontol. 54, 1–8 (1983).
Golub, et al., *Chemical Abstracts*, 100:96203a, (1984).
Engesaeter, et al., *Chemical Abstracts*, 93:142977t, (1980).
Smirnov, I.V., *Chemical Abstracts*, 76:30596, (1969).
Glantz, et al., *Chemical Abstracts*, 91:20178w, (1979).
Myl'lnikova, *Chemical Abstracts*, 86:66138h, (1976).
Dreisbach, et al., "Induction of Collagenase Production in Vibrio B–30", *J. Bacteriology*, vol. 135, No. 2, pp. 521–527, (1978).
Goodman and Gilman, *The Pharmacological Basis of Therapeutics*, 6th edition, p. 961–962, (1980).
Perry, et al., "Systemic Tetracycline in the Treatment of Non–Infected Corneal Ulcers and Persistent Epithelial Defects", *J. Period Res.* 83:20, 185–195 (Abstracts and Artide) (1984).
Gomes, et al., "Tetracycline Inhibit Parathyroid Hormone–Induced Bone Resorption in Organ Culture", School of Dental Medicine Study, SUNY, (Mar. 19, 1984).
"Anti–Plaque Agents", *Pharmacy Times*, 97 (Jul. 1985).
"Periodontal Disease Research, Guide to Dental Health", *Journal of the American Dental Association*, 70–74 (1985).
"British Bio–Technology Group's Collagenase Inhibitor Adjunctive", *F–D–C Reports*, Inc., 13 (1983).
ALZA/P&G Periodontal Disease Partnership:Actisite, *F–D–C Reports*, Inc., 8–9 (1990).
"Zyderm Collagen Treatments", Collagen Corporation, Advertisement, (Dec., 1981).
O'Donovan, J.P., "A Chick Screen to Evaluate Chemical Compounds from Janssen Pharmaceutical for Growth Promotion", Chick Growth Promotion Screen Report (1987).
Katz, S.E., "Is Today's Meat Fit to Eat?", *Chemical and Engineering News*, 80–81 (Mar. 11, 1985).
Golub, et al., Minocycline Therapy Reduces Gingival Collagenolytic Enzyme Activity During Diabetes: A Proposed New Mechanism Of Action, *J. Of Periodontal Research*, 18: 516–526, Abstract, (1983).
Williams et al., Tetracycline Treatment of Periodontal Disease in the Beagle Dog:, *Journal of Periodontal Research*, 16:555–674, (1981).
Brown et al., "Rheumatoid Arthritis in the Gorilla:A Study of Mycoplasma–Host Interaction in Pathogenesis and Treatment", *Comarative Pathology of Zoo Animals*, 259–266, (1980).
Bermah, M.B., "Collagenase and Corneal Ulceration", 8:141–174, (1980).
Addy, et al., "The Development and in Vitro Evaluation of Acrylic Strips and Dialysis Tubing for Local Drug Delivery", *J. Periodonal*, 693–699, (Nov., 1982).
Addy, et al., "Comparison of the Immediate Effects on the Subgingival Microflora of Acrylic Strips Containing 40% Chlorhexdine, Metronidazole or Tetracycline", *Journal of Clinical Periodontology*, 11:379–386, (1984).
Sheridan, P., "Tetracyclines Block Collagenase Activity", *JAMA*, 252, 1989–1990 (Oct. 19, 1984).
Slots, et al., "Periodontal Therapy in Humans, I. Microbiological and Clinical Effects of a Single Course of Periodontal Scaling and Root Planing, and of Adjunctive Tetracycline Therapy," *J. Periodontol.* 50(10):495–509 (Oct. 1979).
Hellden, et al., "The Effect of Tetracycline and/or Scaling on Human Periodontal Disease," *J. Clin. Periodontol*, 6:222–30 (1979).
Herzberg, MC, "Tetracycline as a Therapeutic Adjunct in the Treatment of Periodontal Diseases," *Northwest Dentistry*, 60(3):131–4 (Jun. 1981).
Fasciano, et al., "Periodontal Regeneration with Long Term Tetracycline Therapy," *Quintessence International*, 12(10):1081–8 (Oct. 1981).
Ciancio, et al., "An Evaluation of Minocycline in Patients with Periodontal Disease," *Journal of Periodontology*, 51(9):530–4 (Sep. 1980).
Williams et al., "Subgingival Microflora of Periodontal Patients on Tetracycline Therapy," *Journal of Clinical Periodontology*, 6:210–21 (1979).
Genco, RJ, "Antiobiotics in the Treatment of Human Periodontal Diseases," *J. Periodontol*, 52(9):545–558 (Sep. 1981).
Weeks, DB, "Tetracycline in the Treatment of Periodontal Disease: Review of Current Literature," *J. Am. Dent Assoc.*, 101(6):935–6 (Dec. 1980).
Ciancio, SG "Tetracyclines and Periodontal Therapy," *J. Periodontology* 47(3):155–159 (Mar. 1976).
Gibson, WA "Antibiotics and Periodontal Disease; A Selective Review of the Literature," *Journal of the American Dental Association*, 104(2):213–8 (Feb. 1982).
Kornman, et al., "The Effect of Long Term Low Dose Tetracycline Therapy on the Subgingival Microflora in Refractory Adult Periodontitis," *J. Periodontology* 53(10):604–610 (Oct. 1982).
Langdon, JD "Antiobiotics in General Dental Practice," *British Dental Journal* 136(8):309–16 (Apr. 16, 1974).
Listgarten, et al., "Effect of Tetracycline and/or Scaling on Human Periodontal Disease," *J. Clinical Periodontology*, 5:246–271 (1978).
Mashimo, et al., "In Vitro Evaluation of Antibiotics in the Treatment of Periodontal Disease," *Pharmacol Ther Dent* 6:45–56 (1981).
Scopp, et al., "Tetracycline: A Clinical Study to Determine its Effectiveness as a Long–Term Adjuvant," *J. Periodontology* 51(6):328–330 (1980).

Tanzer, JM Review Article "The Use of Tetracyclines in the Treatment of Periodontal Disease," *J. Conn State Dent Assoc.*, 57(3):105–12 (Aug. 1983).

Weeks, DB "Tetracycline in the Treatment of Periodontal Disease: Review of Current Literature," *Journal—Connecticut State Dental Assoc.* 56:(1)22–4 (Jan. 1982).

Williams, et al., "Subgingival Microflora of Periodontal Patients on Tetracycline Therapy," *J. Clinical Periodontology*, 6:210–221 (1979).

Ciancio et al, "The Effect of Short–Term Administration of Minocycline HCl on Gingival Inflammation and Subgingival Microflora," *J. Periodontol*, 53(9):557–561 (Sep. 1982).

Finch, "Immunomodulating Effects of Antimicrobial Agents," *Journal of Antimicrobial Chemotherapy*, 6:691–694 (1980).

McNamara, et al., "Crevicular Fluid Studies of a Diabetic and Her Non–Diabetic Twin," Program and Abstracts of Papers, *Journal of Dental Research*, Abstract 1038, vol. 58, Special Issue A (Jan., 1979).

Likins, et al., "Effect of Fluoride and Tetracycline on Alveolar Bone Resorption in the Rat," *National Institute of Dental Research, National Institutes of Health* p. 1532 (Jul. 29, 1963).

Guerrant, "Chlortetracycline and Bone Demineralization in the Rachitic Rat," *Proceedings of the Society for Experimental Biology and Medicine*, 113:268–270 (May–Aug.–Sep., 1963).

Dreisbach, et al., "Induction of Collagenase Production in Vibrio B–30," *Journal of Bacteriology*, 135(2):521–527 (Aug. 1978).

Williams, et al., "Tetracycline Treatment of Periodontal Disease in the Beagle Dog," *Journal of Periodontal Research*, 17:358–365 (1982).

Williams, et al., "Preliminary Observation on the Inhibitory Effect of Tetracycline on Alveolar Bone Loss in Beagle Dogs," *J. Periodontal Res.*, 14:341–351 (1979).

Jeffcoat, et al., "Tetracycline Treatment of Periodontal Disease in the Beagle Dog," *Journal of Periodontal Research*, 17:545–551 (1982).

Williams, et al., "Tetracycline Treatment of Periodontal Disease in the Beagle Dog," *Journal of Periodontal Research*, 16:659–665 (1981).

Williams, et al., "Tetracycline Treatment of Periodontal Disease in the Beagle Dog," *Journal of Periodontal Research*, 16:666–674 (1981).

Valcavi, et al., *Chemical Abstracts*, 95:6899h, (1981).

Brandt, et al., *Chemical Abstracts*, 92:163746m, (1979).

Glatz, et al., *Chemical Abstracts*, 91:20178w, (1979).

Muxfeldt, *Chemical Abstracts*, 76:140344j, (1972).

Bitha, et al., *Chemical Abstracts*, 72:43253P, (1970).

Myl'nikova, *Chemical Abstracts*, 86:66138h, (1976).

Plakunov, *Chemical Abstracts*, 80:104410b, (1973).

Goodson, et al., "Monolithic Tetracycline–containing Fibers for Controlled Delivery to Periodontal Pockets," *J. Periodontol.* 54(10):575–579 (Jan. 1983).

"Zyderm Collagen Treatments," Collagen Corporation, Advertisement, (Dec. 1981).

Golub, et al., "Minocycline Therapy Inhibits the Abnormal Gingival Collagenolytic Activity During Experimental Diabetes," *Journal of Dental Research*, 62:290, Abstract 1085, (1983).

Brown et al., "Rheumatoid Arthritis in the Gorilla: A Study of Mycoplasma–Host Interaction of Pathogenesis and Treatment," *Comparative Pathology of Zoo Animals*, 259–266 (1980).

Berman, M.B., "Collagenase and Corneal Ulceration," 8:141–174, (1980).

Addy et al., "The Development and in Vitro Evaluation of Acrylic Strips and Dialysis Tubing for Local Drug Delivery," *J. Periodontal*, 693–699, (Nov. 1982).

Kanig & Goodman, *J. Pharm. Sci.*, 51:77–83 (1962).

Loe and Silness, *Acta. Odont. Scand.*, 21:533–551 (1963).

Raisz, *J. Clin. Invest.*, 44(1):103–116 (1965).

Stern et al., *Proc. Soc. Exptl. Biol. & Med.*, 119:577–583 (1965).

Bissada, et al., *Periodontics*, 4(5):233–240 (1966).

Finestone and Boorujy, *Diabetes*, 16(5):336–340 (1967).

Stralfors, et al., *Archs. Oral. Biol.*, 12:1213–1216 (1967).

Wener, et al., *Endocrinology*, 90(3):752–9 (1972).

Ramamurthy et al., *J. Periodontal Res.*, 9:199–206 (1974).

Golub, et al., "Some Characteristics of Collagenase Activity in Gingival Crevicular Fluid and Its Relationship to Gingival Diseases in Humans," *J. Dent Res.*, 55(6):1049–1057 (Nov.–Dec. 1976).

Gomes, et al., *Calcif. Tiss. Res.*, 19:285–93 (1976).

Crawford, et al., *J. Periodontal Res.*, 13:316–325 (1978).

Golub et al., *J. Dent. Res.*, 57:520–525 (1978).

Golub, et al., *Biochim Biophys. Acta.*, 534:73–81 (1978).

Heijl, et al., *J. Periodontal Res.*, 15:405–419 (1980).

Genco, et al., J. *Dent. Res.*, 60, Special Issue A, Abstract 872 (1981).

Schneir and Golub, (Streptozotocin: Fundamentals and Therapy) ED. M.K. Agarwal, Elsevier/North–Holland Biomed Press, Chapter 12, pp 161–182, 1981.

Sellers and Murphy, *Int. Rev. Conn. Tiss. Res.*, 9:151–189 (1981).

Sodek, et. al., *J. Periodontal Res.*, 16:425–433 (1981).

Nicoll, et al., *Experientia*, 37:315–317 (1981).

Cianciola, et al., *J.A.D.A.*, 104:653–660 (1982).

Golub, et al., *Infect. Immun*, 37:1013–1020 (1982).

Kaplan, et al., *J. Dent. Res.*, 61, Special Issue, Abstract 872 p. 275 (1982).

McNamara et al., *Archs. Oral Biol.*, 27:217–223 (1982).

Ramamurthy and Golub, *J. Periodontal Res.*, 18:23–30 (1983).

Sakamoto and Sakamoto, *J. Dent. Res.*, 62, Special Issue, Abstract 272 p. 680 (1983).

Krook et al., "Experimental Studies on Osteoporosis," *Methods Achiev Exp Pathol;* 7:72–108 (1975).

Bauer, et al., 1983, J. Invest. Dermatol., vol. 81, pp. 162, 163 168.

Berman and Manabe, 1973, Ann. Ophthalmol., Nov., p. 1193.

Golub, et al., 1985, J. Periodontal Res., vol. 20, pp. 12–23.

Welgus and Stricklin, 1983, J. Biol. Chem., vol. 258, p. 12259–12264.

Uitto, et al., 1984, J. Oral. Path., vol. 13, p. 412.

Narayanan and Page, 1983, Collagen Rel. Res., vol. 3, pp. 33 and 54.

Golub, et al., 1985, J. Periodontal. Res., Special Issue, pp. 93–97.

Vater, et al., 1978, J. Clin. Invest., vol. 62, p. 987.

Harris, et al., 1984, *Collagen Rel. Res.*, vol. 4, pp. 504–512.
Cowen, et al., 1985, Biochem. International, vol. 11, p. 273.
Delaisse et al., 1985, Biochem. Biophys. Res. Commun., vol. 133, p. 483.
Golub et al., "Minocycline Reduces Gingival Collagenolytic Activity During Diabetes: Preliminary Observations and a Proposed New Mechanism of Action." *J Periodont Res.*, 18:516–526 (1983).
Perry et al., Systemic Tetracycline in the Treatment of Non–Infected Corneal Ulcers and Persistent Epithelial Defects, 1984 American Academy of Opthlalmology Abstract Submission Form (1984).
Golub, et al., "Minocycline Reduces Gingival Collagenolytic Activity during Diabetes," *Journal of Periodontal Research* 18: 516–526 (1983).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9 and 20 are determined to be patentable as amended.

Claims 1–8 and 10–19, dependent on an amended claim, are determined to be patentable.

New claims 21–28 are added and determined to be patentable.

9. A method in accordance with claim 20 wherein said tetracycline is [6-demethyl-6-deoxy-5-bydroxy-6-methylenetetracycline] *6-demethyl-6-deoxy-5-hydroxy-6-methylenetetracycline.*

20. A method of treating mammal with bone deficiency disease by enhancing bone protein synthesis in said mammal which comprises administering to the mammal an effective amount of a tetracycline *wherein the effective amount of the tetracycline is a sub-antibacterial dose.*

*21. A method in accordance with claim 20 wherein the effective amount is 10 milligrams to about 50 milligrams and the mammal is a human.*

*22. A method in accordance with claim 20 wherein the effective amount is about 5 to 60% of an antibacterial dose.*

*23. A method of treating a human with bone deficiency disease by enhancing bone protein synthesis in said human which comprises administering to the human an effective amount of doxycycline wherein the effective amount of doxycycline is a sub-antibacterial dose.*

*24. A method in accordance with claim 23 wherein the act of administering to the human an effective amount of doxycycline is long term.*

*25. A method in accordance with claim 23 wherein the effective amount is 10 milligrams to about 50 milligrams.*

*26. A method in accordance with claim 23 wherein the effective amount is about 5 to 60% of an antibacterial dose.*

*27. A method in accordance with claim 23 wherein said doxycycline is administered systemically.*

*28. A method in accordance with claim 23 wherein said doxycycline is administered orally.*

* * * * *